United States Patent [19]

Rafter, Jr.

[11] Patent Number: 4,628,749
[45] Date of Patent: Dec. 16, 1986

[54] METHOD AND APPARATUS FOR OBTAINING LIQUID SAMPLES

[75] Inventor: John A. Rafter, Jr., Fullerton, Calif.

[73] Assignee: Chevron Research Company, San Francisco, Calif.

[21] Appl. No.: 701,323

[22] Filed: Feb. 14, 1985

Related U.S. Application Data

[63] Continuation-in-part of Ser. No. 503,471, Jun. 13, 1983, abandoned.

[51] Int. Cl.$^4$ ............................................. G01N 1/20
[52] U.S. Cl. ................................................. 73/863.71
[58] Field of Search ........... 73/863.01, 863.03, 863.71, 73/863.72, 863.81, 863.86, 864, 864.31, 864.51, 864.54

[56] References Cited

U.S. PATENT DOCUMENTS

| | | | |
|---|---|---|---|
| 3,083,577 | 4/1963 | Nelson et al. | 73/863.71 |
| 3,504,549 | 4/1970 | Davis et al. | 73/863.71 |
| 3,638,498 | 2/1972 | Nelms | 73/863.71 |
| 3,780,590 | 12/1973 | Stamm | 73/863.72 |
| 3,798,972 | 3/1974 | Collins, Jr. | 73/863.71 |
| 4,194,398 | 3/1980 | Gastrock | 73/863.71 |

Primary Examiner—Stewart J. Levy
Assistant Examiner—Robert R. Raevis
Attorney, Agent, or Firm—John A. Rafter, Jr.; Edward J. Keeling

[57] ABSTRACT

The present invention provides a method and apparatus for obtaining liquid samples from a system which is under pressure or vacuum.

14 Claims, 7 Drawing Figures

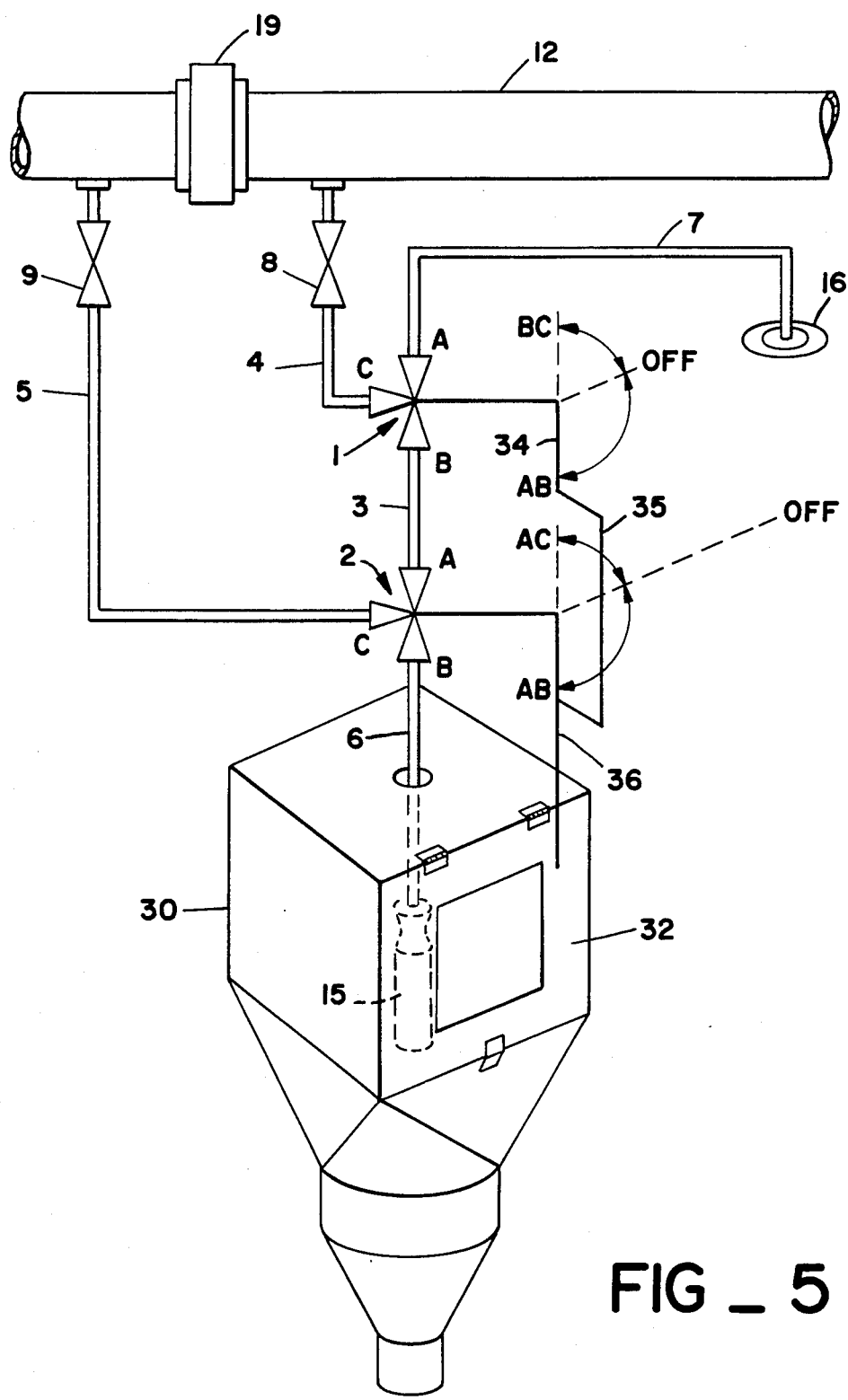
FIG_5

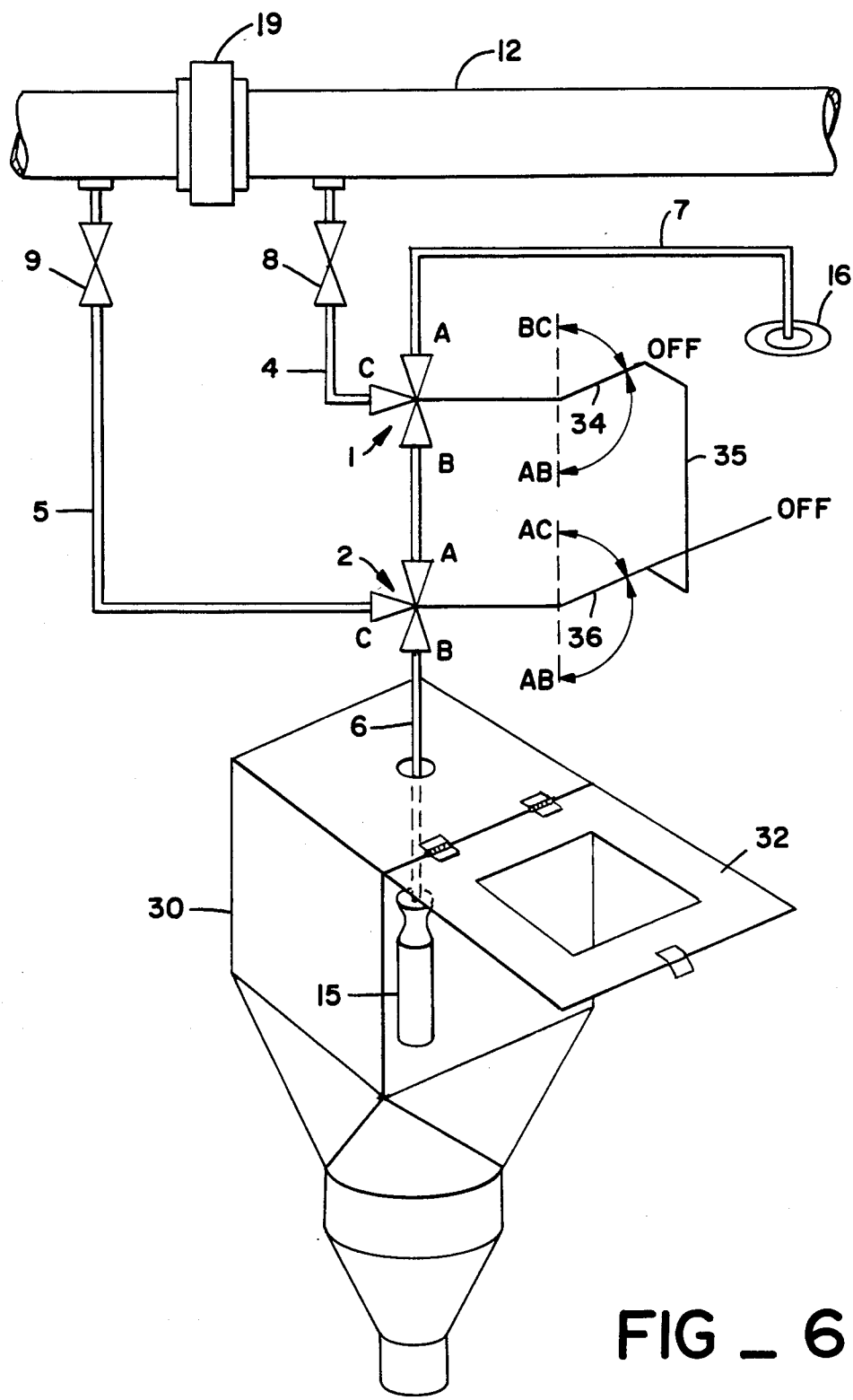
FIG_6

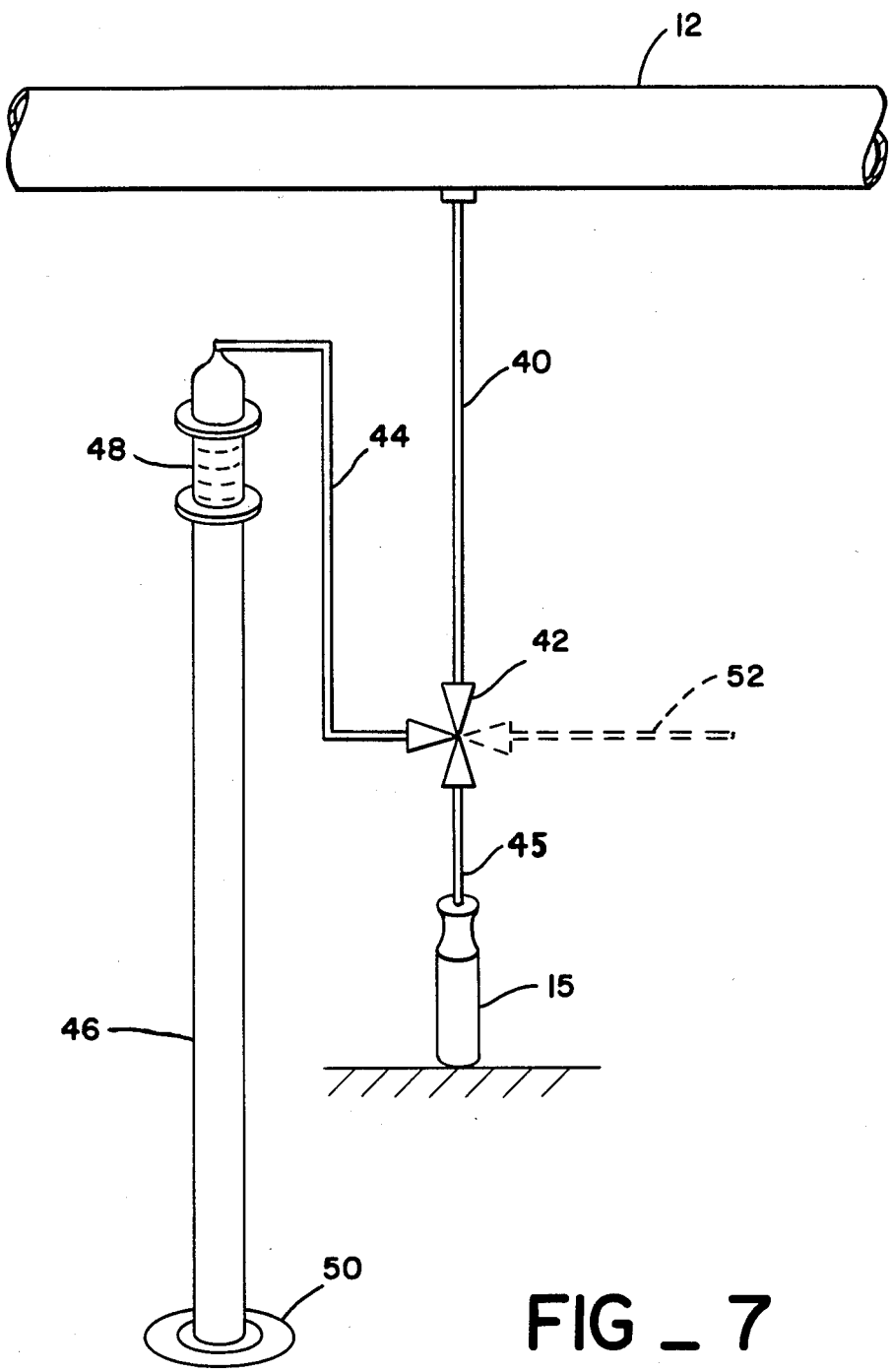
FIG_7

METHOD AND APPARATUS FOR OBTAINING LIQUID SAMPLES

This application is a continuation-in-part of my U.S. application Ser. No. 503,471, filed June 13, 1983 and now abandoned.

BACKGROUND OF THE INVENTION

In industrial plants such as refineries and chemical plants, there are large amounts of fluids flowing through process pipelines. In order to run these plants effectively, it is necessary to know the composition of these fluids. Despite advances in automatic sampling/analysis systems, the prevalent method is to remove a fluid sample and perform lab analysis to determine its composition.

Conventionally, the pipeline is tapped and the fluid is regulated by a throttling valve and poured into a sample bottle. The conventional method is adequate if the fluid pressure is constant and low (less than 15 psig), the fluid is noncorrosive, or the throttling valve performs perfectly. Unfortunately, in refineries and chemical plants the fluid streams are frequently of higher pressures, and the fluids are highly corrosive. These same fluids tend to corrode, erode, or plug the throttling valves, rendering them ineffective. Specialty valves are frequently unavailable, expensive, or unreliable due to their complexity. If the fluid to be sampled is hazardous or produces toxic fumes, the sampling system is usually surrounded by an enclosure to protect the operator from being splashed by the fluid. Despite such precautions, many operators are injured each year when drawing a sample of hazardous fluids (such as acid) because no safe and effective sampling system is readily available.

If the process line is under vacuum rather than positive pressure, the conventional method involves attaching an eductor to draw the fluid. Alternate methods include temporarily shutting down the vacuum source. It is often unfeasible to shut down the vacuum source, and use of an eductor can contaminate the sample or add expense depending on the cost of the driving fluid. It is desirable to have a single sampling system that can obtain samples from a pipeline which is either under vacuum or positive pressure.

SUMMARY OF THE INVENTION

The present invention provides a method and apparatus for safely obtaining a fresh liquid sample from a closed system which is under pressure or vacuum. Most frequently the sample will be extracted from a process line. A pressure drop means is located in the process line producing a high pressure side and a low pressure side therein. One opening of a primary three-way valve is operably connected to the process line on one side of the pressure drop means and one opening of a secondary three-way valve is operably connected to the process line on an opposite side of the pressure drop means to which the primary three-way valve is connected. A flow line is provided and includes a vertically oriented pipe section having an upper portion connected to a second opening of the primary three-way valve and a lower portion connected to a second opening of the secondary three-way valve. A drain line is connected to the third opening of the primary three-way valve. A sample line is connected from a third opening of the secondary three-way valve and extends downward to a sample container.

Operating means are provided for the primary three-way valve and the secondary three-way valve to selectively and alternately permit flow (1) from the process line through the primary three-way valve, through the flow line, through the secondary three-way valve and into the process line and (2) from the drain line through the primary three-way valve, through the flow line, through the secondary three-way valve and into the sample line.

Frequently a pressure drop source such as a pump or an orifice meter already exists in the process line. In accordance with the present invention, the apparatus inlet is connected to the process line on the high pressure side of the pressure drop source and the apparatus outlet is connected to the process line on the low pressure side thereby permitting recirculation of the fluid and conservation of product. If there is no pressure drop source readily available, or one cannot be installed, the apparatus outlet can be routed to drain for disposal as an effective alternative if the process line is under positive pressure. Block valves are provided on both the high pressure connection and the low pressure connection of the apparatus to permit complete isolation of the apparatus.

In the method of the present invention, a pressure drop is established in a process line and a portion of flow of liquid from high pressure side of the process line is diverted and circulated through the apparatus to ensure a hot, indicative sample. As the fluid is circulated through the apparatus, the valves are closed trapping a volume of fluid between them in a flow line which acts as a sample-retaining reservoir. Typically the flow line is vertically oriented and the piping is configured such that the fluid is trapped above the position where the sample will be collected. Once the pressure on the trapped fluid is relieved (e.g., by opening the high side valve to drain), the low side valve is opened allowing the trapped fluid to proceed by gravity flow into a sample container.

Additional design features ensure operator safety. The three-way valves may be connected in order to operate in unison to prohibit opening the secondary three-way valve to the sample line when the primary three-way valve is open to the process line. Access to the sample container may be inhibited when the secondary three-way valve is open to the sample line. The inhibiting may be accomplished by locating the secondary three-way valve such that its handle blocks the door on the enclosure which surrounds the sample container when the valve is open to the sample line.

PRINCIPAL OBJECT OF THE INVENTION

The principal obJect of the present invention is to provide a method and apparatus for safely drawing a fresh indicative liquid sample from a system, such as a process pipeline, into an open container. Further objects and advantages of the present invention will become apparent from the following description and the drawings which are made part of this specification.

BRIEF DESCRIPTION OF THE DRAWINGS

FIG. 5 shows the apparatus of the present invention with the valve handle inhibiting access to the sample enclosure.

FIG. 6 shows the apparatus of the present invention with the sample line isolated from the process line and the hinged door of the sample enclosure free to open.

FIG. 7 shows an alternative embodiment of the present invention requiring only one valve.

DETAILED DESCRIPTION OF THE PREFERRED EMBODIMENT

For convention, any numeral common between different drawings will refer to the same component throughout. For example, secondary three-way valve 2 refers to the same component in FIGS. 2, 3, 4, 5 and 6.

Figure 1:
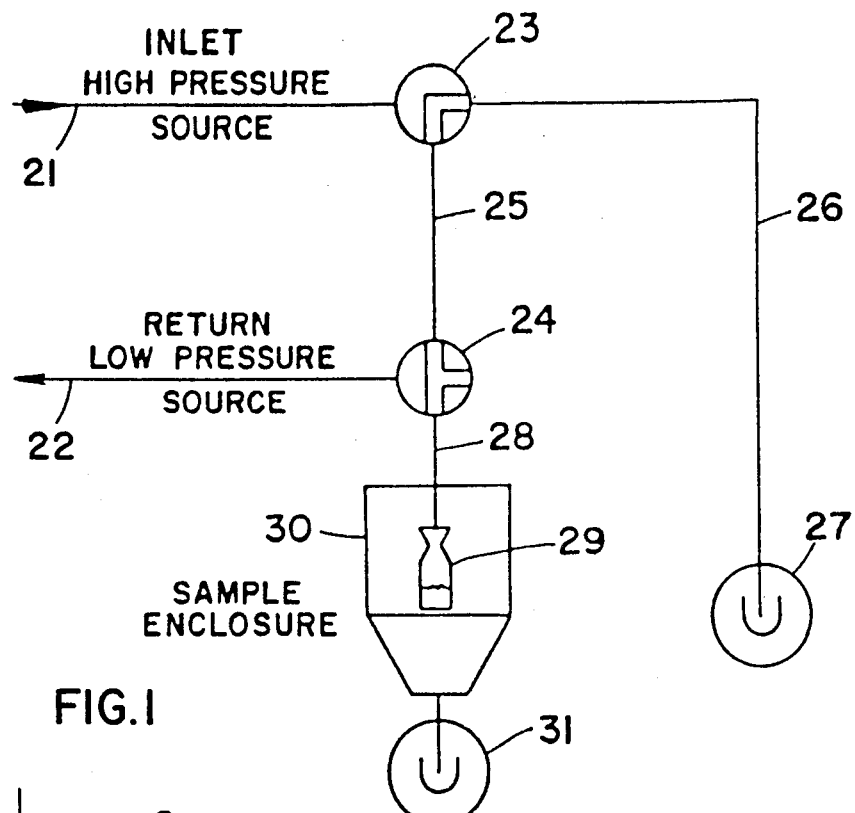
FIG. 1 is a schematic view of the apparatus assembled in accordance with the present invention.

The apparatus shown in FIG. 1 diverts a portion of flow of liquid from the sampling location 21, through primary valve 23 and flow line 25, and then through secondary valve 24 to a lower pressure location 22.

The diverted flow is stopped thereby trapping a portion of the liquid in the flow line 25. By opening the flow line 25 at the upper portion through primary valve 23 to drain 7 via drain line 26, pressure on the trapped liquid is relieved to atmospheric pressure. By opening the flow line 25 at the lower portion through secondary valve 24 to sample line 28, a sample of liquid flows into the sample container 29. The sample container can be placed in sample enclosure 30 for further safety. Spillage within the enclosure 30 will be disposed in drain 31.

Figure 2:
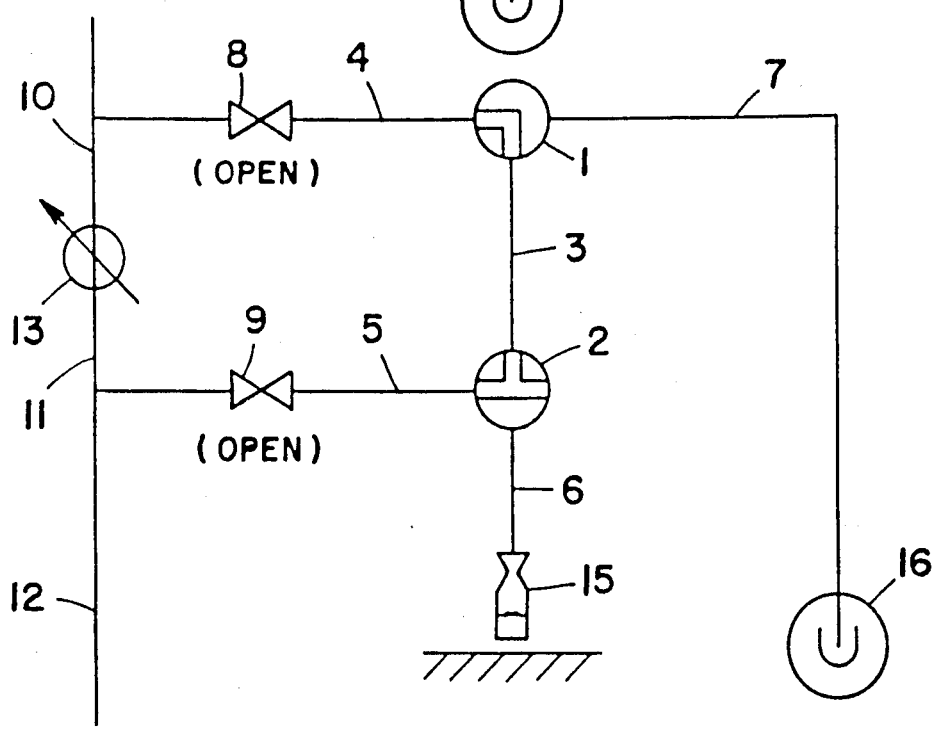
FIG. 2 is a schematic view of the apparatus of the present invention arranged in a circulating flow mode.
Figure 3:
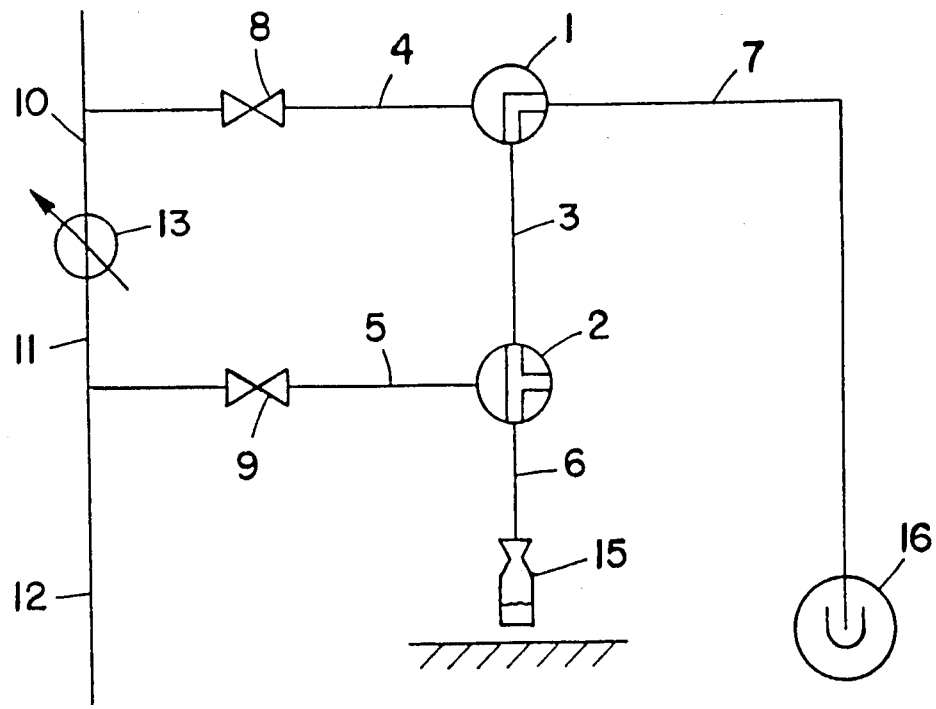
FIG. 3 is a schematic view of the apparatus of the present invention in a sample collecting mode.

An example of the apparatus of the present invention extracting a fluid sample from a pump discharge line is generally shown in FIGS. 2 and 3. An industrial plant has a process line 12 with a pump 13 from which a sample needs to be drawn into sample container 15. An inlet line 4 is connected into pump discharge line 10 through block valve 8. An outlet line 5 is connected into pump suction line 11 through block valve 9. Block valves 8 and 9 are in the open position except when isolating the apparatus from the process line 12.

When the primary and secondary valves are actuated into position as shown in FIG. 2, fluid circulates from 10, the high pressure side of pump 13 through block valve 8 entering the apparatus inlet 4, through primary valve 1, through flow line 3, through secondary valve 2, exiting the apparatus outlet 5 through block valve 9, returning to process line 12 at the low pressure side of the pump. In FIG. 3 the fluid trapped in flow line 3 is emptied into the sample container 15 by relieving the pressure on system when primary valve 1 is opened to drain 16 through drain line 7, thereby allowing the fluid to proceed by gravity flow through secondary valve 2 and sample line 6 to the sample container 15.

The simplest operating means consists of manual actuation of a pair of three-way valves. Normally the valve size will range from $\frac{1}{2}$" to $1\frac{1}{2}$", but any valve size consistent with the pipe size will perform adequately. Typical small sample valves of conventional methods (needed to effectively throttle a fluid) have a tendency to plug or corrode with corrosive fluids. In addition, many company specifications do not permit pipe or valve sizes below $\frac{3}{4}$" in refinery or chemical service. The present invention accommodates standard size three-way valves, including lined valves such as Tufline Plug valves manufactured by XOMOX Corp., 4444 Cooper Rd., Cincinnati, Ohio, which are less susceptible to corrosion or plugging and are available as off-the-shelf items. The present invention can use the standard size valves because the fluid is not throttled. Without waste, the apparatus isolates a specific volume of the fluid from the process line and then relieves the pressure. The sample is then drawn by gravity flow. Exposure to the operator from the hazards of fluid vapor or splattering liquid is greatly reduced.

Figure 4:
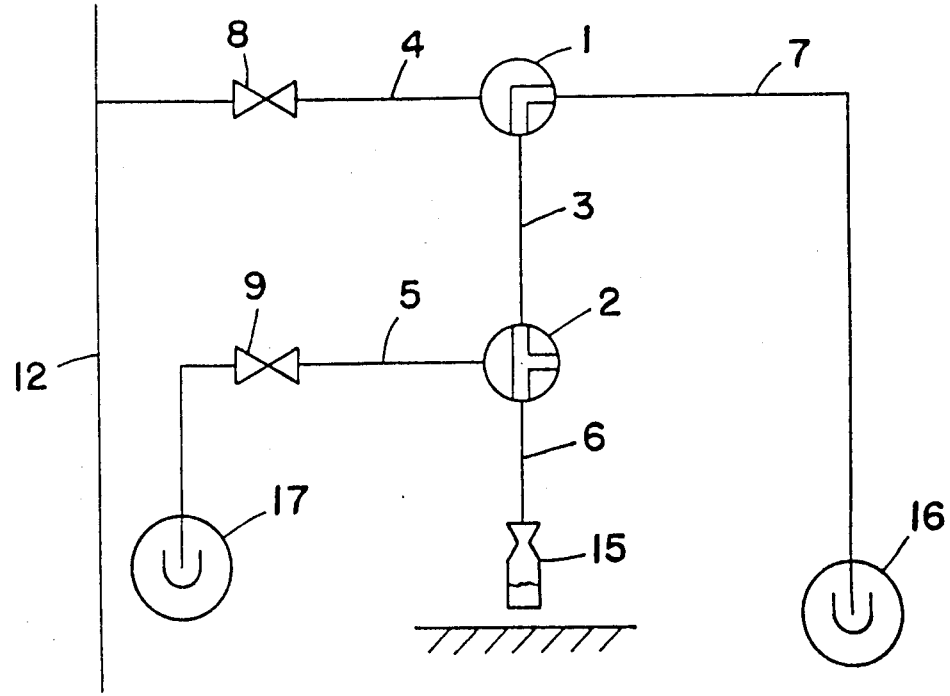
FIG. 4 shows an alternate embodiment where a sampling location in a system under positive pressure is the apparatus inlet and the outlet is a drain.

There are instances where a system to be sampled does not have a location at a lower pressure than that of the sampling location to permit recirculation. FIG. 4 shows an embodiment similar to the device of FIGS. 2 and 3 except the sampling location (device inlet) 12 is under positive pressure and the device outlet 5 is to a drain 17.

All numerals in FIGS. 5 and 6 are identical. FIGS. 5 and 6 are similar to FIGS. 2 and 3 except the pressure drop is created by orifice meter 19 (of FIGS. 5 and 6) in place of pump 13 (of FIGS. 2 and 3). FIGS. 5 and 6 illustrate two examples of means being responsive to positions of the secondary three-way valve 2 whereby fluid samples are withdrawn into the sample container 15 from the flow line 3 only when flow line 3 is not in communication with process line 12. One example of means being responsive comprises a means to inhibit access to the sample container 15. When the secondary three-way valve 2 is open to sample line 6 as shown in FIG. 5, the pivoting valve handle 36 on secondary three-way valve 2 blocks the door 32 of the sample enclosure 30 thereby inhibiting access to sample container 15. Door 32 cannot be opened when secondary three-way valve 2 is open to sample line 6. FIG. 6 shows secondary three-way valve 2 in an off position and door 32 is free to open unblocked by pivoting valve handle 36. Other means such as electrical switches may provide suitable alternative means to inhibit access.

Though manual actuation of the valve handles provides the simplest operating means, alternate operating means and schemes can simplify the operation of the apparatus. FIGS. 5 and 6 demonstrate a mechanical linkage 35 connected between the handles 34 and 36 of three-way valves 1 and 2 to permit valve actuation by a single motion. Mechanical linkage 35 is another example of means being responsive to positions of the secondary three-way valve 2. The mechanical linkage 35 provides a means to prohibit opening the secondary three-way valve 2 to the sample container 15 when the primary three-way valve 1 is open to the process line 12. Various pneumatic and electrical control devices may also be adapted to the invention allowing remote or automatic sampling thereby further enhancing operability and safety. For example, a pneumatic control scheme may be installed to perform the same function as the mechanical linkage 35, simultaneously actuating both three-way valves 1 and 2, thereby prohibiting opening the secondary three-way valve 2 to the sample container 15 when the primary three-way valve 1 is open to the process line 12.

FIG. 7 shows an alternative apparatus using a multi-port valve 42 with one opening connected to the sampling location of the process line 12 through inlet line 40. A seal leg line 44 has an upper portion connected to a drain line 46 and a lower portion connected to a second opening of the multi-port valve 42. A third opening of the multi-port valve is connected to a sample line 45 extending downward to a sample container 15. FIG. 7 shows drain line 46 extending to a drain 50, however, drain line 46 may just dump into a bucket or reservoir.

Its purpose is to provide drainage and venting of the upper portion of seal leg line 44 thereby permitting fluid to flow by gravity out of seal leg line 44 through multiport valve 42 and to the sample container 15. A three-way valve may satisfy the function of multi-port valve 42 and have three operating positions: (1) flush product from inlet line 40 through and filling seal leg line 44; (2) draw sample from seal leg line 44 through sample line 45; and (3) an off position.

To ensure vacuum on seal leg 44 is broken and prevent siphoning, drain pipe 46 may be enlarged to a pipe diameter size larger than that of the seal leg line 44. Optionally a sight glass 48 may be installed on the drain line 46 to observe fluid to be sampled and to observe whether vacuum is indeed broken. Another sight glass (not shown) may be installed in seal leg line 44 to observe fluid.

Optionally a fourth opening on the multi-port valve 42 may be connected to a return line 52 which returns to a place in the process system which is at a lower pressure than the process inlet 40, thereby recycling process fluid back into the process system. The inlet line 40 may extend a significant distance, say from pipeway fifteen feet overhead. Rather than disposing all the product while flushing the inlet line 40, product may be conserved by recirculating fluid back through return line 52. A four-way valve may satisfy the function of multi-port valve 42 and may have four operating positions: (1) recirculate from inlet line 40 to return line 52; (2) flush product from inlet line 40 through and filling seal leg line 44: (3) draw sample from seal leg line 44 through sample line 45; and (4) an optional off position.

OTHER ADVANTAGES OF THE INVENTION

Since the apparatus does not depend on positive fluid pressure for its operation, samples may be drawn from a process line under vacuum by the same procedure as from a process line under pressure. The invention is a single apparatus which handles all types of fluid sampling, reducing the possibility of operator confusion and the resulting hazards.

Since the invention is assembled from standard components, the apparatus can be readily installed and repaired by field personnel. When repairs are required, the apparatus is conveniently isolated by closing valves 8 and 9 without shutting down the process system. In addition, the operators are familiar with the standard components and require little orientation or training in the operation of the apparatus. The same familiarity improves safety and confidence in the invention.

Although only specific embodiments of the present invention have been described in detail, the invention is not limited to, but is meant to include all embodiments within the scope of the amended claims.

What is claimed is:

1. An apparatus for obtaining a fluid sample from a process line comprising:
    a process line;
    a pressure drop means in said process line with a high pressure side and a low pressure side;
    a primary three-way valve with one opening operably connected into said process line on one side of said pressure drop means;
    a secondary three-way valve with one opening operably connected into said process line on an opposite side of said pressure drop means to which said primary three-way valve is connected;
    a flow line having an upper portion connected to a second opening of said primary three-way valve and a lower portion connected to a second opening of said secondary three-way valve;
    a drain line connected to a third opening of said primary three-way valve;
    a sample container;
    a sample line connected from a third opening of said secondary three-way valve and extending downward to said sample container;
    operating means for said primary three-way and said secondary three-way valve to selectively and alternately permit flow (1) from said process line through said primary three-way valve, through said flow line, through said secondary three-way valve, and into said process line; and (2) from said drain line through said primary three-way valve, through said flow line, through said secondary three-way valve and into said sample line; and
    a means to inhibit access to said sample container when said secondary valve is in a prescribed position open to said flow line,
    wherein said means to inhibit comprises a pivoting valve handle on said secondary three-way valve, said secondary three-way valve having a location such that said pivoting valve handle inhibits access to said sample container when said secondary three-way valve is in a prescribed position open to said process line.

2. The apparatus of claim 1 further comprising:
    a sample enclosure with a hinged door on said sample enclosure which is blocked by said pivoting handle on said secondary three-way valve when said secondary three-way valve is in a prescribed position open to said process line.

3. The apparatus of claim 1 where sizing of said flow line determines a volume of process fluid obtained in the fluid sample.

4. The apparatus of claim 1 further comprising a means to prohibit opening said secondary three-way valve to said sample container when said primary three-way valve is in a prescribed position open to said process line.

5. The apparatus of claim 4 wherein said means to prohibit comprises a mechanical linkage between said primary three-way valve and said secondary three-way valve such that both valves are operated in unison.

6. The apparatus of claim 4 wherein said means to prohibit comprises an automatic control means of said primary three-way valve and said secondary three-way valve such that both valves are operated in unison.

7. An apparatus for obtaining a fluid sample from a sampling location in a process system under positive pressure comprising:
    a multi-port valve with one opening operably connected into the sampling location;
    a seal leg line having an upper portion and a lower portion, said lower portion operably connected to a second opening of said multi-port valve;
    a drain pipe line operably connected end-to-end to said upper portion of said seal leg line and extending downward to a drain, wherein said drain pipe line is a larger diameter pipe size than said seal leg line to prevent siphoning of fluid sample from the seal leg line down the drain pipe line;
    a sample container; and a sample line operably connected to a third opening of said multi-port valve and extending downward to said sample container.

8. The apparatus of claim 7 wherein said multiport valve is a three-way valve.

9. The apparatus of claim 7 wherein said multiport valve is a four-way valve.

10. The apparatus of claim 9 further comprising:
a recirculation line operably connected to a fourth opening of said multi-port valve and running to a return location in the process system which has a lower pressure than that at the sample location.

11. The apparatus of claim 7 further comprising:
a means to inhibit access to the sample container when said multi-port valve is open to said sample line.

12. The apparatus of claim 7 further comprising: a sight glass in said seal leg line.

13. The apparatus of claim 7 further comprising: a sight glass in said drain pipe line.

14. An apparatus for obtaining a fluid sample from a sampling location in a process system under positive pressure comprising:
a multi-port valve with one opening operably connected into the sampling location;
a seal leg line having an upper portion and a lower portion, said lower portion operably connected to a second opening of said multi-port valve;
a pipe drain line operably connected to said upper portion of said seal leg line and extending downward to a drain;
a sample container;
a sample line operably connected to a third opening of said multi-port valve and extending downward to said sample container; and
a pivoting valve handle on said multi-port valve, said multi-port valve having a location such that said pivoting valve handle inhibits access to said sample container when said multi-port valve is open to said sample line.

* * * * *